(12) United States Patent
Wickham et al.

(10) Patent No.: US 6,629,528 B1
(45) Date of Patent: Oct. 7, 2003

(54) APPARATUS FOR SUPPLYING BREATHABLE GAS

(75) Inventors: Peter John Deacon Wickham, Five Dock (AU); Alexander Virr, Balmain (AU); Ian Malcolm Smith, Westleigh (AU); Muditha Pradeep Dantanarayana, Baulkham Hills (AU); Stanley Clark, Warriewood (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/931,909

(22) Filed: Aug. 20, 2001

Related U.S. Application Data

(63) Continuation of application No. 09/268,758, filed on Mar. 16, 1999, now Pat. No. 6,302,105.

(30) Foreign Application Priority Data

Mar. 17, 1998 (AU) .............................................. PP2401

(51) Int. Cl.$^7$ .............................................. A61M 16/00
(52) U.S. Cl. .............................. 128/204.18; 128/204.22
(58) Field of Search ...................... 128/204.18, 204.19, 128/204.21, 204.23, 205.27, 200.27, 200.28, 201.25, 201.29, 204.11, 205.12, 205.22, 204.26, 202.22; 417/410.1, 423.14; 73/19.04, 861

(56) References Cited

U.S. PATENT DOCUMENTS

| | | | | |
|---|---|---|---|---|
| 3,193,261 A | * | 7/1965 | Nesbitt | ........................ 261/142 |
| 3,528,781 A | * | 9/1970 | Gelfman et al. | .............. 261/29 |
| 4,076,021 A | | 2/1978 | Thompson | |
| 4,080,112 A | | 3/1978 | Zimmerman | |
| 4,152,099 A | | 5/1979 | Bingler | |
| 4,299,784 A | | 11/1981 | Hense | ......................... 261/78 |
| 4,320,755 A | | 3/1982 | Flint et al. | |
| 4,350,646 A | | 9/1982 | Baus | |
| 4,458,609 A | * | 7/1984 | Tofte | ........................... 111/119 |
| 4,767,378 A | * | 8/1988 | Obermann | .................... 464/29 |
| 4,935,656 A | | 6/1990 | Kawamura | |
| 4,971,052 A | | 11/1990 | Edwards | |
| 5,356,272 A | | 10/1994 | Nagata et al. | |
| 5,383,470 A | * | 1/1995 | Kolbly | ........................ 600/538 |
| 5,393,207 A | | 2/1995 | Maher et al. | |
| 5,645,054 A | | 7/1997 | Cotner et al. | |
| 5,803,720 A | | 9/1998 | Ohara et al. | |
| 5,857,348 A | | 1/1999 | Conry | |
| 5,924,851 A | | 7/1999 | Obata et al. | |
| 5,949,001 A | * | 9/1999 | Willeke | ..................... 73/865.5 |
| 6,074,180 A | | 6/2000 | Khanwilkar | |

FOREIGN PATENT DOCUMENTS

| | | | |
|---|---|---|---|
| EP | 0 470 535 A2 | 2/1992 | |
| GB | 1 343 738 | 1/1974 | |
| GB | 2043877 A | * 10/1980 | ........... G01F/1/075 |
| WO | WO 97/10350 | 10/1997 | |

* cited by examiner

Primary Examiner—Glenn K. Dawson
Assistant Examiner—Mital Patel
(74) Attorney, Agent, or Firm—Nixon & Vanderhye P.C.

(57) ABSTRACT

An apparatus (10) for supplying breathable gas is disclosed. The apparatus (10) includes a main housing (12), a sub-housing (14), having a gas flow path (28) between a gas inlet (16) and a gas outlet (18), a motive power source (22) within the main housing (12) and an impeller (30) within the sub-housing (14) in fluid communication between the gas inlet (16) and the gas outlet (18). The impeller (30) is adapted to releaseably engage the motive power source (22) external the gas flow path (28) and the sub-housing (14) is releasably connectable to said main housing.

Also disclosed is a method of cleaning, sterilising or disinfecting the gas flow path (28) of the breathable gas supply apparatus (10). The method of cleaning comprising the steps of removing the sub-housing (14) from the main housing (12) cleaning, sterilising, disinfecting or replacing the sub-housing (14) and connecting the sub-housing (14) to the main housing (12).

7 Claims, 10 Drawing Sheets

APPARATUS FOR SUPPLYING BREATHABLE GAS

This is a Continuation of U.S. application Ser. No. 09/268,758 filed on Mar. 16, 1999 now U.S. Pat. No. 6,302,105, the entirety of which is hereby incorporated herein by reference.

FIELD OF THE INVENTION

The present invention relates to an apparatus for supplying breathable gas to a human used in, for example, the Continuous Positive Airway Pressure (CPAP) treatment of Obstructive Sleep Apnea (OSA), other respiratory diseases/disorders such as emphysema or the application of assisted ventilation.

BACKGROUND OF THE INVENTION

CPAP treatment of Obstructive Sleep Apnea (OSA) involves the delivery of a breathable gas (generally air) pressurised above atmospheric pressure to a patient's airways via a conduit and a mask. CPAP pressures of 4 cm $H_2O$ to 22 cm $H_2O$ are typically used for treatment of OSA, depending on patient requirements. Treatment pressures for assisted ventilation can range of up to 32 cm $H_2O$ and beyond, again depending on patient requirements.

For either the treatment of OSA or the application of assisted ventilation or similar, the pressure of the gas delivered to patients can be constant level, bi-level (in synchronism with patient breathing) or auto setting in level. Throughout this specification reference to CPAP is intended to incorporate a reference to any one of, or combinations of, these forms of pressurised gas supply.

A disadvantage of existing CPAP gas supply apparatus, especially those used in hospitals and the like, is the danger of biological contamination and disease/virus/bacteria transfer. More particularly, there can be a significant reverse flow during heavy expiration and/or coughing and biological material exhaled by a patient can be deposited in the gas supply apparatus and transferred to another patient who uses the same machine. Further, a patient continually using the same machine can be re-infected by a prior condition.

Hitherto, CPAP apparatus have basically comprised a closed outer casing surrounding internal components. Components inside, and constituting part of, the gas flow path include the gas inlet, inlet filter, impeller, outlet muffler and gas outlet. Components outside the gas flow path include control electronics, power regulators and motor. As a result, present CPAP apparatus have a gas flow path that is extremely difficult to clean/sterilise without the time consuming dismantling and removal of all the "gas flow path" components. Further, without disassembly, common sterilisation procedures such as autoclaving will damage the circuit boards and other electrical components.

An attempt to solve the above problem involves incorporating a bacteriological filter into the gas flow path adjacent the gas outlet to prevent biological material being forced back into the machine and any such material leaving the machine and being inhaled by the patient. However, these filters are expensive and add a significant resistance to the air path requiring larger and noisier fans and motors. A more restricted air path also represents a major difficulty to administering bi-level CPAP treatment due to the higher inspiratory air flow requirements of patients with advanced respiratory disease. Moreover, it is difficult to produce a biological filter which can trap very small biological particles such as viruses and spores that is still able to pass the required amount of air with an acceptable pressure drop, as decreasing filter pore size decreases hydraulic permeability.

It is an object of the present invention to substantially overcome or at least ameliorate one or more of the above prior art deficiencies.

SUMMARY OF THE INVENTION

Accordingly, in a first aspect, the present invention provides an apparatus for supplying breathable gas, the apparatus including:

a main housing;

a sub-housing having a gas flow path between a gas inlet and a gas outlet;

a motive power source within the main housing;

an impeller within the sub-housing in fluid communication between the gas inlet and the gas outlet, the impeller adapted to releaseably engage the motive power source external the gas flow path, wherein the sub-housing is releasably connectable to said main housing.

Preferably, the sub-housing includes one or more of an inlet filter, outlet muffler, gas flow rate sensing means, gas pressure sensing means or gas supply vent valve assembly.

Desirably, the motive power source is an electric motor.

Desirably also, the main housing includes one or more of a power supply and control system for the motor.

The motor preferably includes an output shaft terminating in an engaging formation adapted to releasably engage a complimentary engaging formation provided on the impeller.

The main housing preferably also includes a removable or pivotable lid adapted to restrain the sub-housing adjacent the main housing. In a preferred form, the lid includes acoustic shielding to reduce the emission of noise generated by the impeller and motor.

In a preferred embodiment, the gas flow rate sensing means includes a flexible flap in the gas flow path, the flap disposed between a light source and a linear image sensor respectively disposed either side of the flap and external to the gas flow path, whereby the amount of light incident on the image sensor is proportional to the deflection of the flap which is proportional to the gas flow rate.

In another preferred embodiment, the gas pressure sensing means includes a flexible membrane having one side in fluid communication with the gas flow path and an opposite side abutting a force probe coupled to a force transducer, whereby the displacement of the probe and transducer is proportional to the displacement of the membrane which is proportional to the gas pressure.

In yet another preferred embodiment, the gas vent valve assembly includes a gas venting conduit in fluid communication with the gas flow path, the gas venting conduit adapted to be selectively restricted by a cam abutting the gas venting conduit exterior, whereby varying the cam position varies gas passing through the gas venting conduit which varies the flow rate of remaining gas leaving the gas outlet.

Preferably, the motive power source includes a disk having magnets thereon and the impeller includes magnets mounted thereon, the disk magnets and the impeller magnets being adapted to attract.

Alternatively, the motive power source includes a disk having magnets thereon and the impeller includes a magnetically attractable plate mounted thereon, the disk magnets and the plate being adapted to attract.

In another embodiment, the motive power source includes a disk having magnets thereon and the impeller includes a non-ferrous metal plate, or a plate formed from a non magnetically attractable material having non-ferrous metal therein, mounted thereon.

In a further embodiment, the impeller includes a shaft having ferrite or other magnetic material mounted thereon and the main housing includes electric motor windings adapted to surround the ferrite or other magnetic material.

In a second aspect, the present invention discloses a method of cleaning, sterilising or disinfecting the gas flow path of the breathable gas supply apparatus of the first aspect, said method comprising the steps of:

(a) removing the sub-housing from the main housing, and (b) cleaning, sterilising, disinfecting or replacing the sub-housing; and (c) connecting the sub-housing to the main housing.

BRIEF DESCRIPTION OF THE DRAWINGS

Preferred embodiments of the invention will now be described by way of example only, with reference to the accompanying drawings in which.

DETAILED DESCRIPTION OF THE PREFERRED EMBODIMENTS

Figure 1:
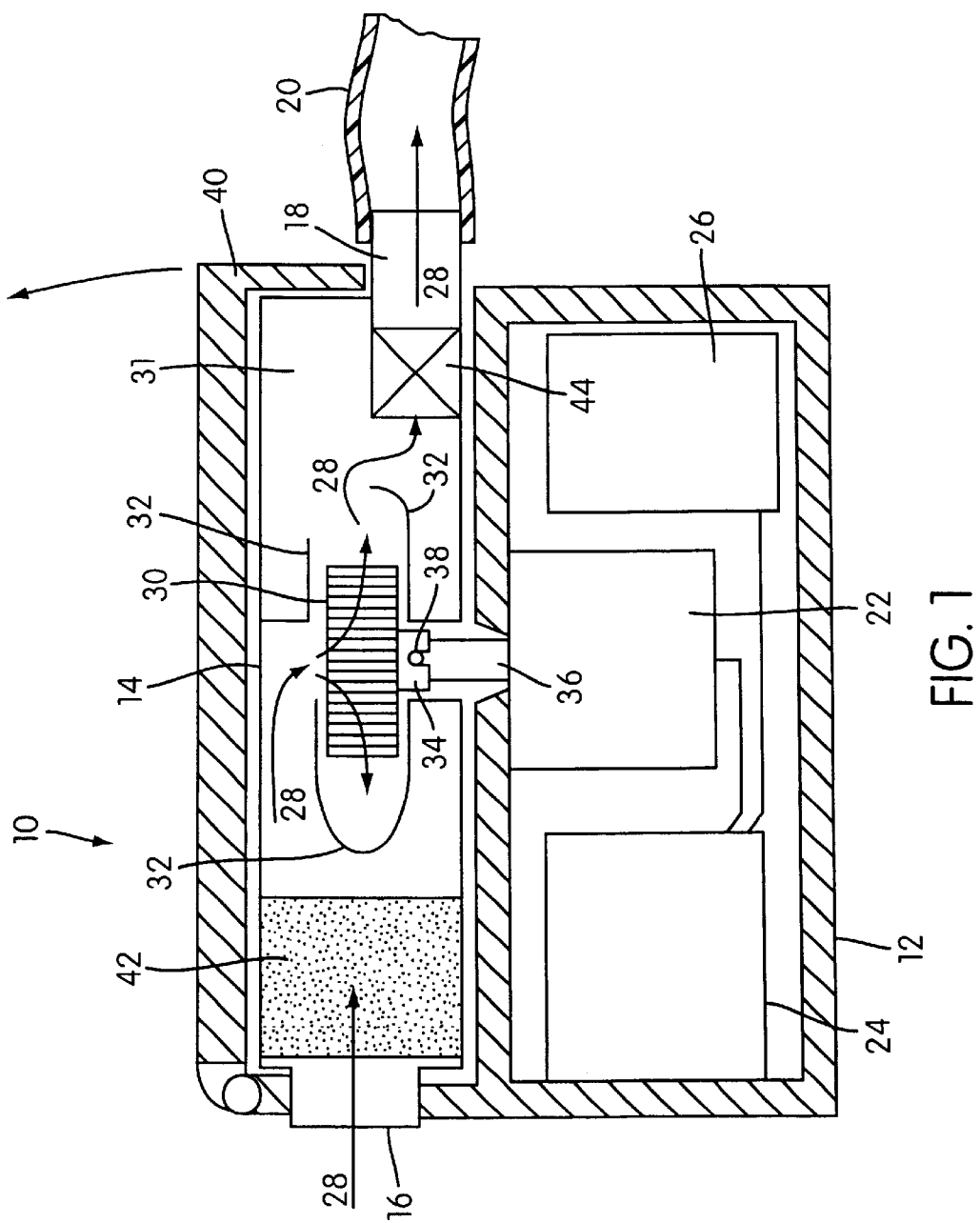
FIG. 1 is a cross sectional side view of a first embodiment of an apparatus according to the invention in an assembled state.

Referring firstly to FIG. 1, there is shown an apparatus 10 for supplying breathable gas in accordance with a first embodiment of the invention. The apparatus 10 includes a main housing 12 and a sub-housing 14. The sub-housing 14 has a gas inlet 16 and a gas outlet 18 which is connected to a face mask (not shown) by a flexible conduit 20 to supply a breathable gas (eg. air) to a patient.

The main housing 12 includes a motive power source in the form of an electric motor 22 which receives power from an electrical power source 24. An electronic control system 26 controls the power source 24 to thus control the speed of the motor 22.

The inlet 16 and the outlet 18 represent the beginning and end respectively of a gas flow path through the sub-housing 14. The passage of gas along the flow path is represented by arrows 28. The sub-housing 14 also includes an impeller 30 disposed in the flow path in fluid communication between the inlet 16 and outlet 18 and partitions 32 which form a housing around the impeller 30 and an expansion chamber-type outlet muffler 31.

The impeller 30 includes a female engagement formation in the form of slotted cylinder 34 which is adapted to releasably engage to the male engagement formation on the end of motor shaft 36 in the form of projections 38 (only one shown). It is important to note that the engagement between the impeller 30 and the motor shaft 36 is external the gas flow path. Other engaging arrangements such as splines, dogs, clips, non contact magnetic couplings or the like can also be used.

The main housing 12 includes a hinged lid 40 which is adapted to releasably clamp the sub-housing 14 to the main housing 12. The lid 40 can include acoustic shielding to reduce the emission of noise generated by the impeller 30 and the motor 22.

Figure 2:
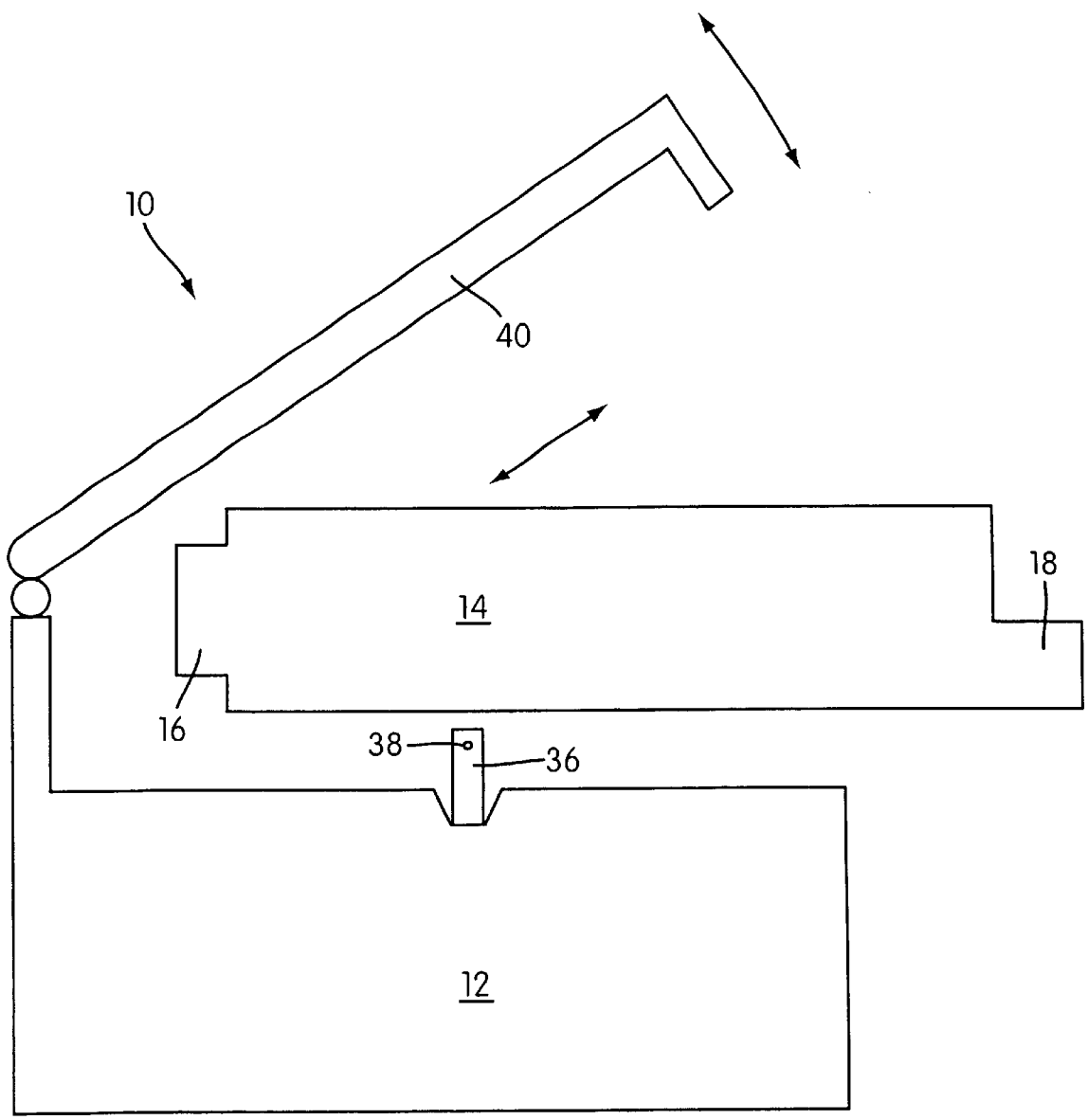
FIG. 2 is a side view of the apparatus shown in FIG. 1 in a disassembled state.

FIG. 2 shows the lid 40 in an open position in which the motor shaft 36 is disengaged from the impeller 30 allowing the sub-housing 14 to be removed from the main housing 12.

The removability of the sub-housing 14 represents a major improvement over prior art devices as the sub-housing 14 contains most of the "gas flow path" components of the breathable gas supply apparatus 10 that can come into contact with airborne particles from atmosphere or from the patient being treated and it can easily be removed, disposed and replaced with a clean, sterile or disinfected sub-housing 14. Alternatively, the sub-housing 14 can be removed, cleaned, sterilised or disinfected and then reinstalled.

The protruding portion of the shaft 36 may also contact airborne particles and removing the sub-housing 14 provides easy access to this component for cleaning, sterilising or disinfecting.

In a preferred form, the sub-housing 14 is moulded from plastics material such as polypropylene, polycarbonate, acrylic, aluminium, polyurethane foam (such as 1SF1350 type manufactured by URETEC) or other like high temperature resistant biocompatible materials which can be easily cleaned, sterilised or disinfected using common procedures such as autoclaving.

Depending on the requirements of the breathable gas supply apparatus 10, the sub-housing 14 can also include an inlet filter 42 (see FIG. 1).

Figure 3:
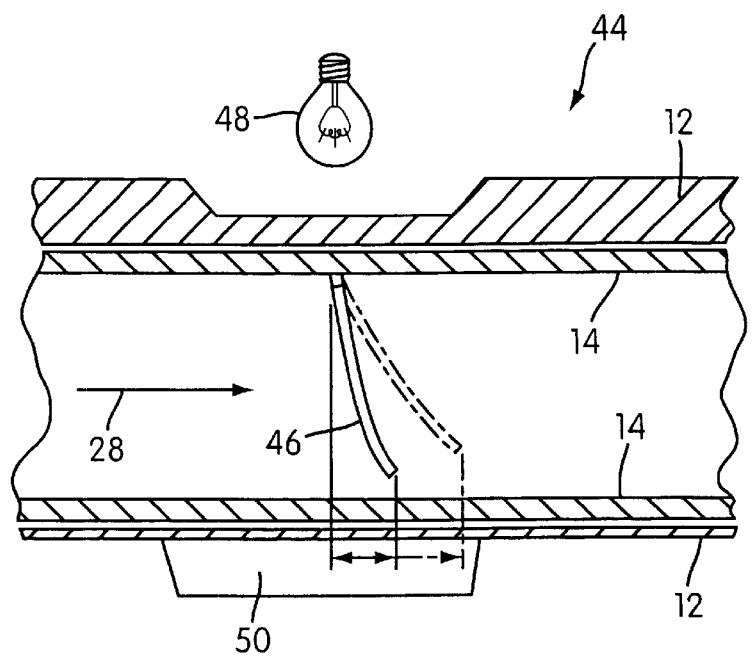
FIG. 3 is a sectional side view of a gas flow rate sensing mean which can be incorporated into the apparatus of FIG. 1.

In some breathable gas supply apparatus, such as those used for bi-level CPAP, it is desirable to measure the flow rate of gas delivered to the patient. An embodiment of a gas flow rate sensing means 44 suitable for use with the removable sub-housing 14 is shown in FIG. 3 and includes a flexible flap 46 disposed in the gas flow path between a light source 48 and a linear image sensor 50. The greater the gas flow passing the flap 46 causes proportionally greater deflection of the flap 46 and thus a proportionally greater amount of occluding of light from the light source 48 that falls on the linear image sensor 50. In this way, the output of the sensor 50 can be calibrated to be indicative of flap deflection and thus gas flow rate.

With this arrangement, only the flexible plastic flap 46 is within the flow path and is therefore cleaned etc or replaced along with the sub-housing 14. The expensive and delicate light source 48 and sensor 50 are external of gas flow path, free from contamination risk and remain fixed to the main housing 12.

Figure 4:
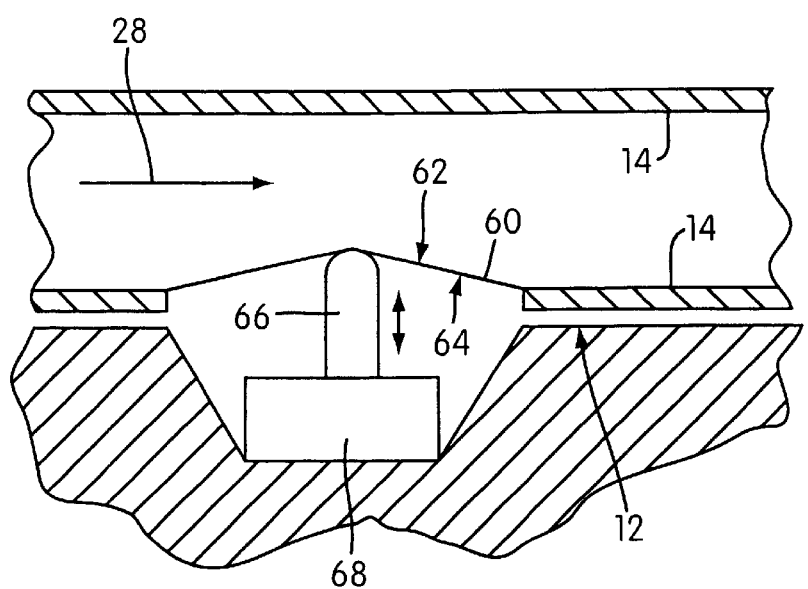
FIG. 4 is a side view of a gas pressure sensing means which can be incorporated into the apparatus of FIG. 1.

In some breathable gas supply apparatus, it is also necessary or desirable to be able to measure the pressure of the gas delivered to the patient. An embodiment of a pressure sensing arrangement suitable for use with the removable sub-housing 14 is shown in FIG. 4 and includes a flexible membrane 60 having one side 62 in fluid communication with the flow path and an opposite side 64 abutting a force probe 66 coupled to a force transducer 68. Increases and decreases in gas pressure cause the membrane 60 to expand and contract respectively and displace the force probe 66 thereby altering the output of the transducer 68. Thus, it is possible to calibrate a relationship between gas pressure and transducer output.

As with the gas flow rate sensing means 44, this embodiment is suitable for use with the removable sub-housing 14 as the membrane remains fixed to the sub-housing 14 and may be easily cleaned, sterilised or disinfected or replaced along with the sub-housing 14. The probe 66 and transducer 68 are external the flow path, free from contamination risk and remain fixed to the main housing 12.

Figure 5:
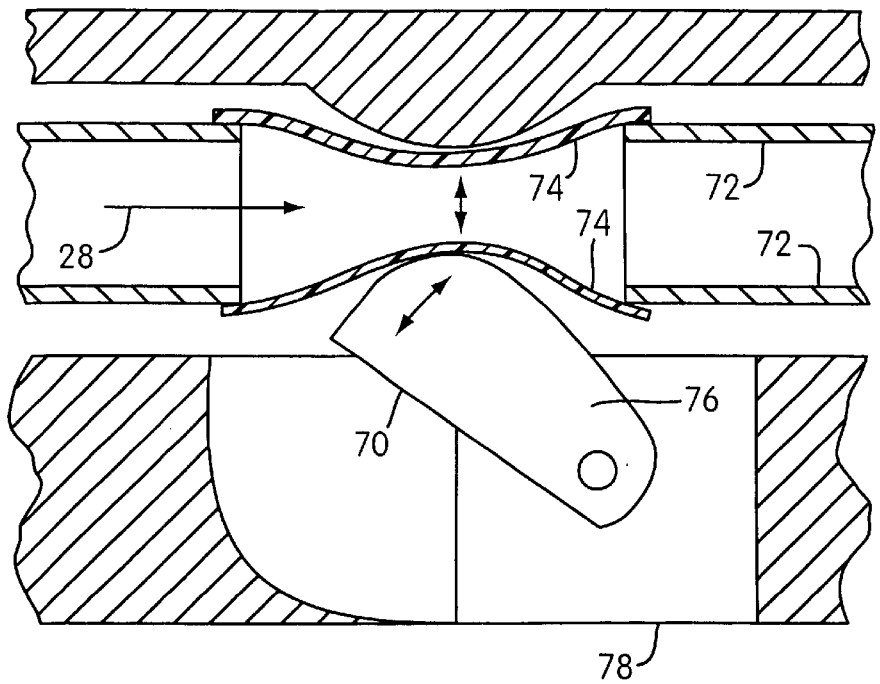
FIG. 5 is a side view of a portion of a gas vent valve assembly which can be incorporated into the apparatus of FIG. 1.

Bi-level CPAP is usually administered by either altering the impeller motor speed in synchronism with patient breathing or using a vent valve assembly to control the ratio of gas vented to atmosphere to gas delivered to the patient. FIG. 5 shows an embodiment of a gas vent valve assembly 70 suitable for use with the removable sub-housing 14. The vent valve assembly 70 includes gas venting conduit 72 in fluid communication with the gas outlet 18 shown in FIG. 1 and having a flexible portion 74. A pivotable cam 76 controlled by a motor 78 is used to selectively restrict the internal cross section of the flexible portion 74 and thereby control the proportion of gas vented to atmosphere from the system to regulate the pressure of remaining gas supplied to the patient. As with the embodiments of FIGS. 3 and 4, the venting conduit 72 and flexible portion 74 can be removed, cleaned and replaced with the sub-housing 14, whilst the cam 76 and motor 78 remain external the flow path and fixed to main housing 12.

Figure 6:
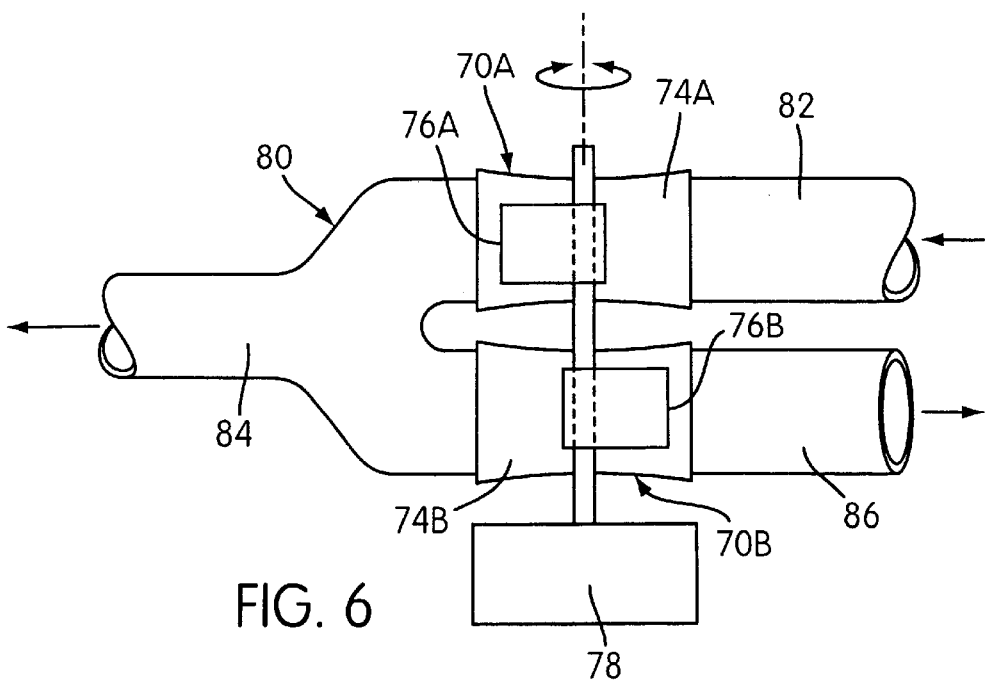
FIG. 6 is a top view of another gas vent valve assembly which can be incorporated into the apparatus of FIG. 1.

FIG. 6 shows another embodiment of a gas vent valve assembly, suitable for use with the removable sub-housing 14, which controls the pressure of gas supplied to the patient with two pivotable cams 76A and 76B which restrict respective flexible portions 74A and 74B. The cams 76A, 76B form part of two vent valve assemblies 70A and 70B of a similar nature to the assembly 70 shown in FIG. 5. The cams 76A, 76B are linked so that upon rotation by motor 78 one flexible portion is progressively restricted while the other is progressively enlarged and vice-versa.

In the embodiment shown, the cams 76A, 76B are installed adjacent a Y shaped conduit 80 which comprises three conduit portions 82, 84 and 86 which are in fluid communication with the impeller 30, outlet 18 and atmosphere respectively. If a low gas supply pressure to the patient is desired, the valve assemblies 70A, 70B are used to simultaneously restrict the gas flow in the conduit portion 82 from the flow generator while increasing the gas flow to the atmosphere through conduit portion 86. If a high gas supply pressure to the patient is desired, the pivotable cams 76A and 76B are turned in the opposite direction to simultaneously restrict the venting of gas to the atmosphere through conduit portion 86 and increase the gas supplied to the patient through conduit portion 84.

The embodiment of FIG. 6 provides an apparatus for supplying breathable gas that uses relatively less power and causes less wear on the flow generator motor and bearings. The gas flow vented to atmosphere is also reduced which thereby reduces the associated noise of the gas passing through the vent to atmosphere.

Figure 7:
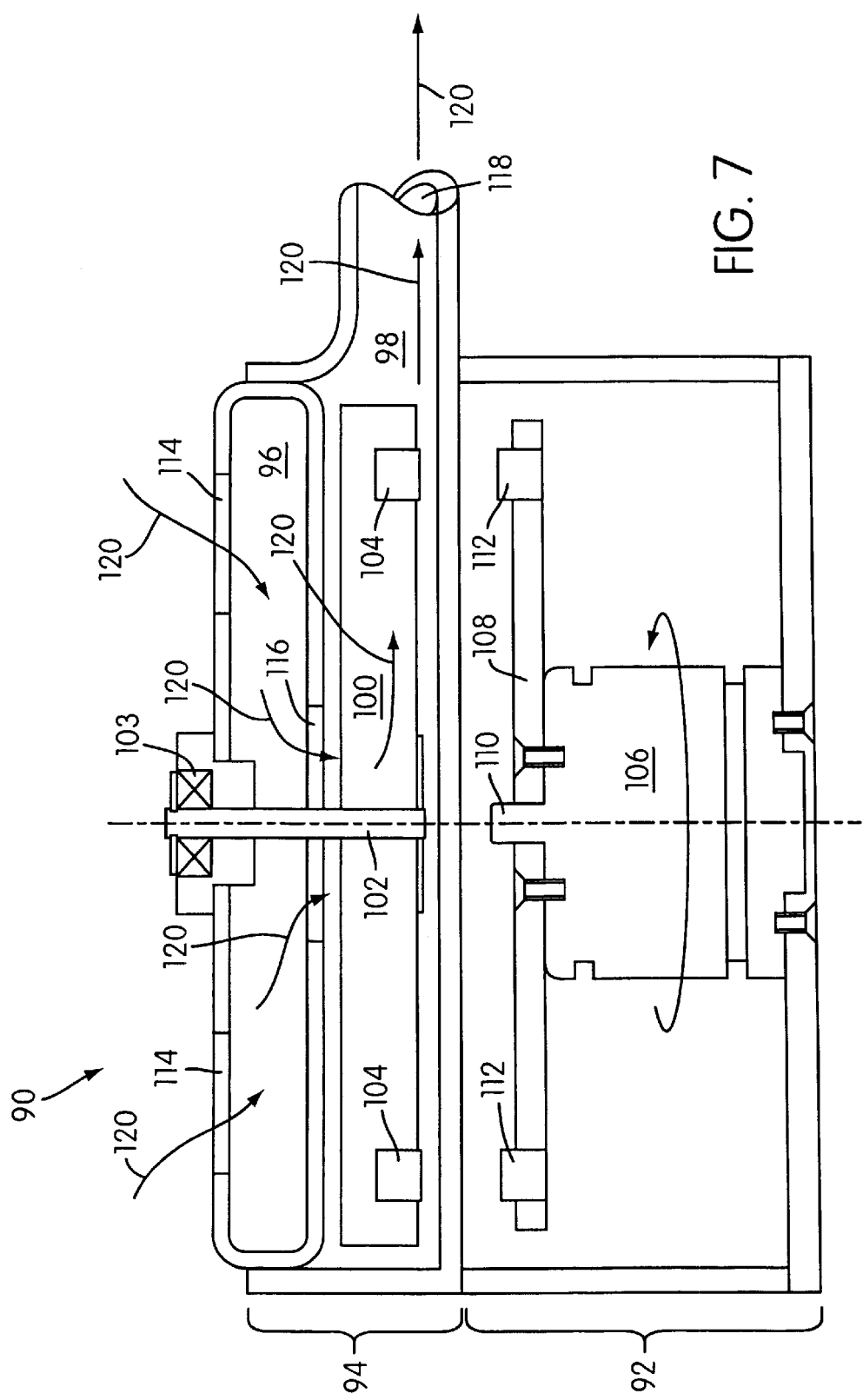
FIG. 7 is a schematic sectional side view of a second embodiment of an apparatus according to an invention in an assembled state.

FIG. 7 shows an apparatus 90 for supplying breathable gas in accordance with a second embodiment of the invention. Similar to the first embodiment, the apparatus 90 includes a main housing 92 and a sub-housing 94.

The sub-housing 94 has an inlet chamber 96 and an outlet chamber 98 within which is located an impeller 100. The impeller 100 is mounted on the bottom end of a shaft 102. The top end of the shaft 102 is retained in a bearing assembly 103 mounted to the inlet chamber 96. The impeller 100 also includes a number of magnets 104 mounted near its periphery. Six equiangularly spaced magnets are used in the preferred embodiment.

The main housing 92 includes a motive power source in the form of an electric motor 106. A disk 108 is attached to the output shaft 110 of the motor 106. Magnets 112 are mounted near the periphery of the disk 108 in general alignment with the magnets 104 provided on the impeller 100. The magnets 104 and 112 are configured to attract each other.

Energising the motor 106 causes the disk 108 to rotate. The attraction between the magnets 104 and 112 causes the impeller 100 to rotate also. The rotation of the impeller 100 draws air through upper openings 114 in the inlet chamber 96, through to a lower opening 116 and into the impeller 100. Pressurised air is then forced through outlet 118 of the outlet chamber 98, as indicated by arrows 120. The outlet 118 of the sub-housing 94 is connected to a face mask (not shown) by a flexible conduit (not shown) to supply the air (or other breathable gas) to a patient.

As with the first embodiment, the sub-housing 94, which contains all of the components that can come into contact with particles from atmosphere or from the patient being treated, can be easily and quickly removed from the main housing 92 by overcoming the attraction between the magnets 104 and 112. As with the first embodiment, this allows the sub-housing 94 to be easily removed and disposed and replaced with a new clean, sterile or disinfected sub-housing 94 or removed, cleaned, sterilised or disinfected and then reinstalled.

Figure 12:
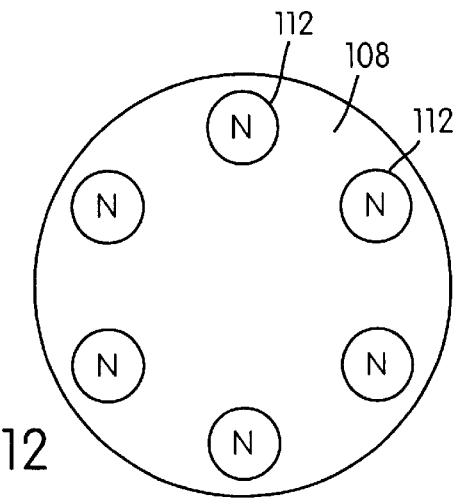
FIG. 12 is a schematic top view of a first magnet arrangement used in the embodiment shown in FIG. 7.
Figure 13:
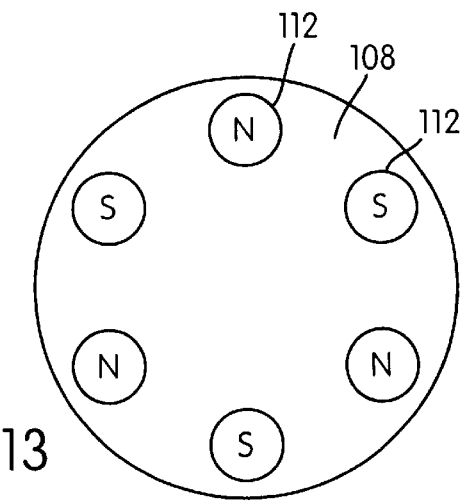
FIG. 13 is a schematic top view of a second magnet arrangement used in the embodiment shown in FIG. 7.
Figure 14:
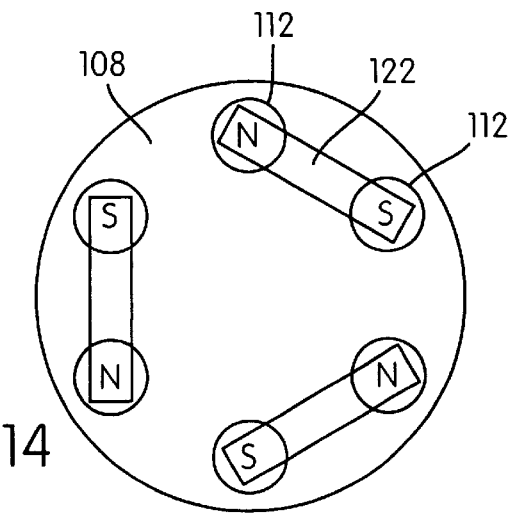
FIG. 14 is a schematic top view of a third magnet arrangement used in the embodiment shown in FIG. 7.
Figure 15:
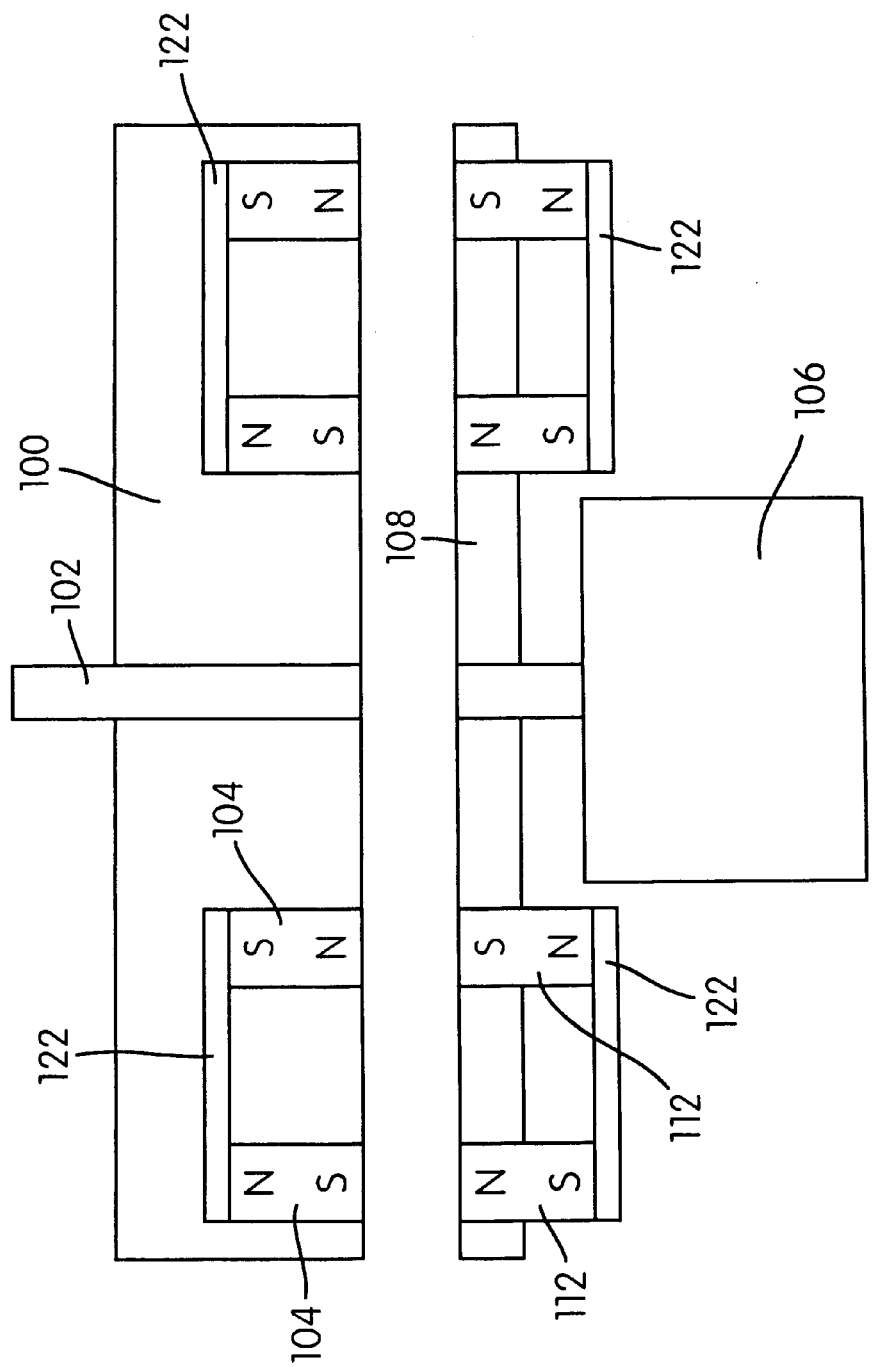
FIG. 15 is a schematic cross sectional side view of the magnet arrangement shown in FIG. 14.

FIGS. 12, 13, and 14 and 15 respectively show three preferred arrangements of the magnets 112 on the disk 108. In FIG. 12, the magnets 112 have their poles aligned in one direction (North being shown). In FIG. 13, the magnets 112 are arranged with adjacent magnets 112 having alternating poles. In FIGS. 14 and 15, the magnets 104, 112 have alternating poles grouped in pairs by magnetic bridges 122. The magnets 104 on the impeller 100 are arranged with opposite (ie. attracting) polarity to those of the disk 108.

Figure 8:
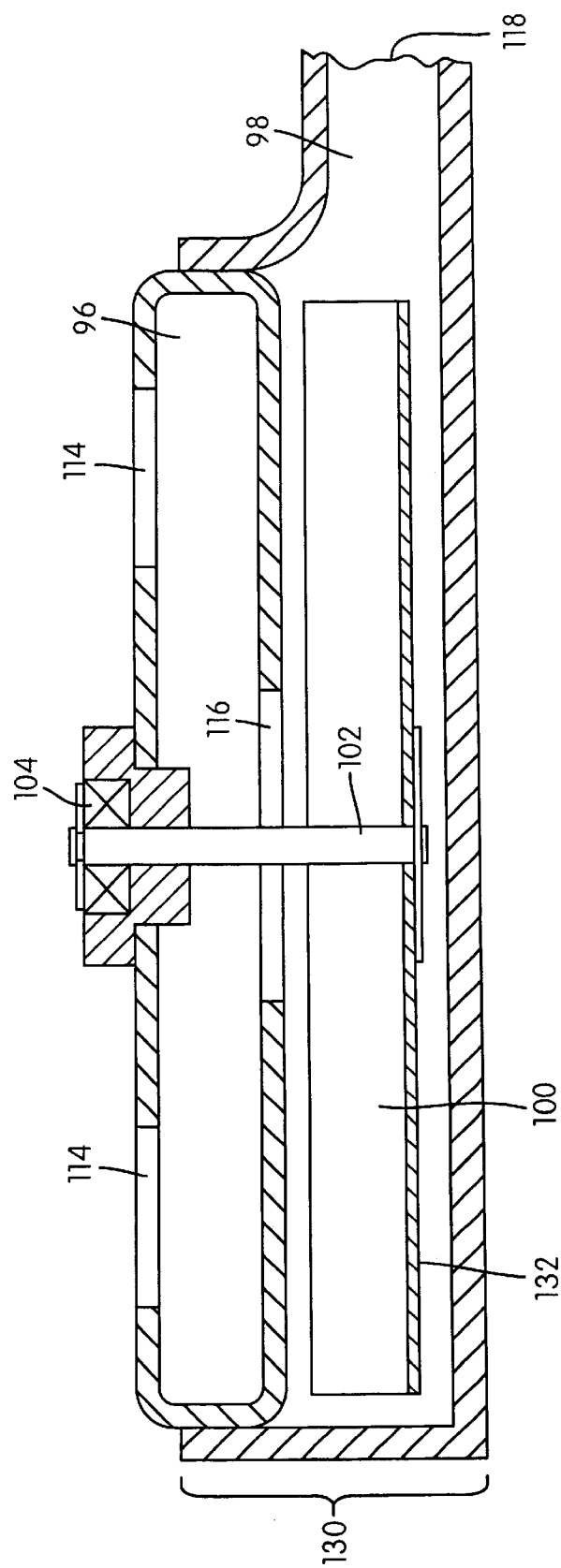
FIG. 8 is a schematic cross sectional side view of an alternative form of sub-housing which can be used with the main housing shown in FIG. 7.

FIG. 8 shows an alternative form of a sub-housing 130 that can also be used with the main housing 92 shown in FIG. 7. The sub-housing 130 is very similar to the sub-housing 94 and like reference numerals have been used to denote like features. However, in the sub-housing 130, the impeller 100 includes a plate 132 on its underside rather than the magnets 104 shown in the embodiment of FIG. 7.

In one form, the plate 132 is made from a material that is attracted to magnets, for example steel. As with the embodiment shown in FIG. 7, when the disk 108 rotates the attraction between the magnets 112 and the plate 132 causes rotation in the impeller 100 also.

In another form, the plate 132 is made of a non-ferrous metal, for example Aluminium. In this form, when the disk 108 rotates the magnets 112 produce a magnetic field which passes through the plate 132 and causes eddy currents in, and rotation of, the plate 132 and thus the impeller 100 also. Alternatively, the plate 132 can be formed from a non magnetically attractive material, for example a polymer, having a non-ferrous metal, such as Aluminium, therein.

Figure 9:
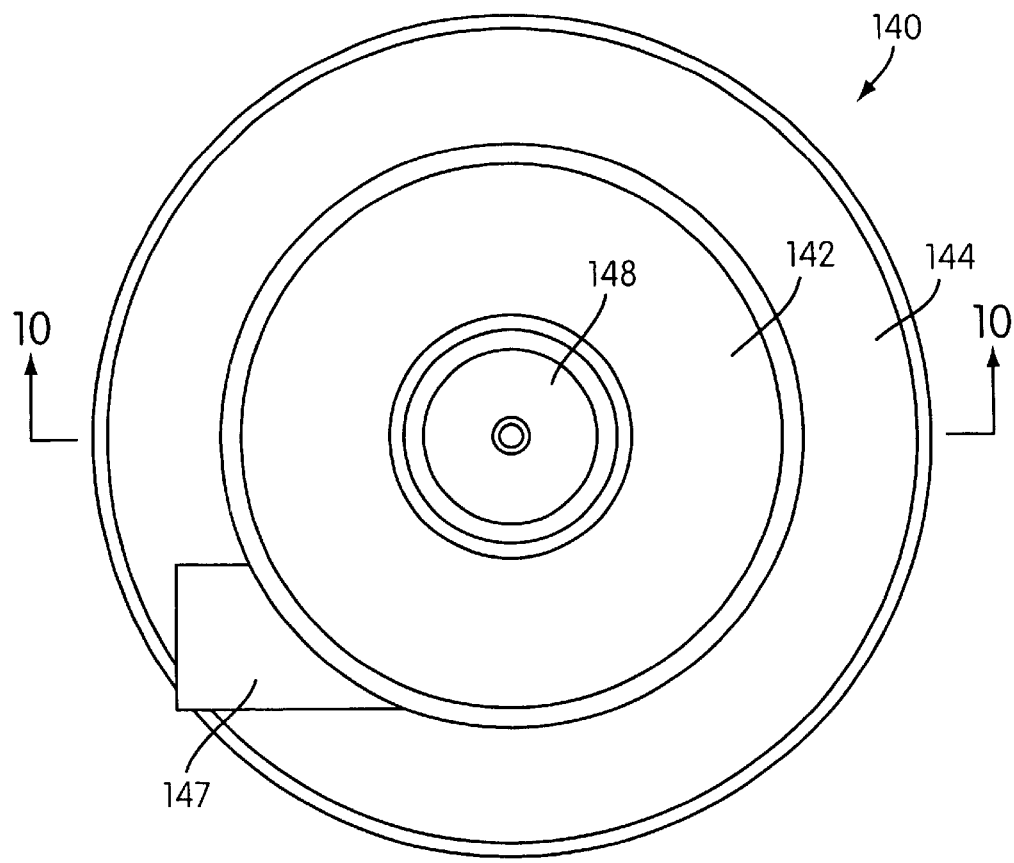
FIG. 9 is a top view of an impeller housing and motor assembly adapted for use with an apparatus according to the invention.
Figure 10:
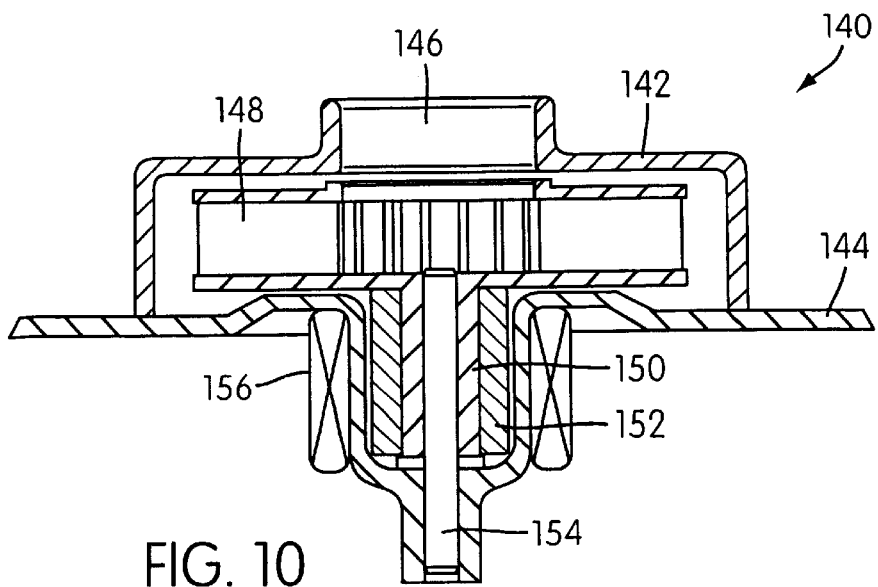
FIG. 10 is a cross sectional side view of the assembly shown in FIG. 9 along line 10—10 of FIG. 9.
Figure 11:
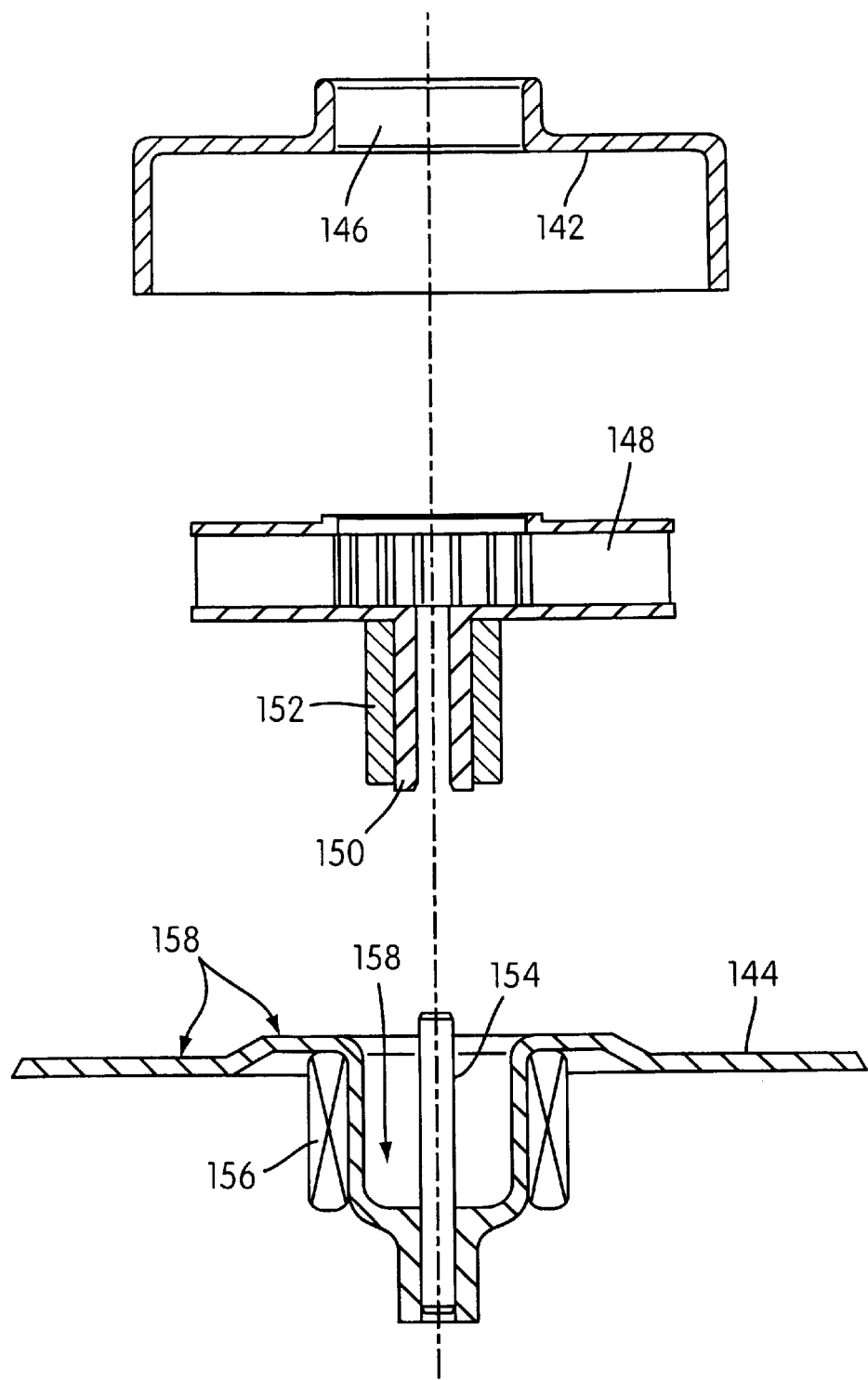
FIG. 11 is an exploded view of the housing shown in FIG. 10.

FIGS. 9 to 11 show an impeller housing and motor assembly 140 suitable for use in an apparatus for supplying breathable gas in accordance with another embodiment of the invention. In this embodiment, the assembly 140 includes an upper part 142 which constitutes a sub-housing and a lower part 144 which constitutes a main housing. The upper part 142 includes an inlet 146, an outlet 147 and an impeller 148 mounted therein.

As best shown in FIG. 11, the impeller 148 includes a hollow shaft 150 to which is mounted ferrite material 152. The lower part 144 includes a shaft 154 which is adapted to be received within the interior of the hollow shaft 150 to form a bearing. The lower part 144 also includes motor windings 156 that surround the ferrite material 152. Energising the motor windings 156 creates a magnetic field which causes the ferrite material 152, and thus the impeller 148, to rotate and draw air from the inlet 146 to the outlet 147 for supplying gas to the patient by the means previously described.

Similar to the earlier embodiments, the upper part 142 and the impeller 148 can be removed for cleaning, sterilising, disinfecting or replacement without dismantling the rest of the apparatus to which the lower part 144 is attached. Removing the upper part 142 and the impeller 148 also provides easy access to external surfaces 158 of the lower part 144 for cleaning, sterilising or disinfecting.

In a variation (not shown) of the embodiment shown in FIGS. 9 to 11, gas is bled from the impeller 148 into the interface between the hollow shaft 150 and the shaft 154 to float the impeller 148 (in the manner of an air bearing) and thus reduce noise.

Although the invention has been described with reference to the preferred embodiments, it would be appreciated by those skilled in the art that the invention may be embodied in many other forms.

We claim:

1. A sub-housing received within a housing of an apparatus structured to supply breathable gas, the sub-housing including:

a gas flow path between a gas inlet and a gas outlet;

a gas flow rate sensor positioned adjacent the gas outlet; and an impeller in fluid communication with and positioned between the gas inlet and the gas outlet, wherein the impeller is structured and configured to be releasably engaged with a shaft associated with an electric motor that is disposed exterior to the housing, whereby rotation of the shaft causes rotation of the impeller; and wherein the gas flow rate sensor includes a flexible flap in the gas flow path, the flap disposed between a light source and a linear image sensor respectively disposed either side of the flap and external to the gas flow path, whereby the amount of light incident on the image sensor is proportional to the deflection of the flap which is proportional to the gas flow rate.

2. A sub-housing as claimed in claim 1, wherein the gas flow rate sensor decreases an effective diameter of the gas flow path.

3. A sub-housing as claimed in claim 1, wherein the impeller includes a first coupling structure structured and configured to releasably engage a second coupling structure formed on the shaft to thereby couple the impeller to the electric motor.

4. A sub-housing as claimed in claim 3, wherein the first coupling structure includes a cylinder having a slot formed thereon and the second coupling structure includes a projection formed on the shaft, the projection being received within the slot to thereby releasably engage the first coupling structure and the second coupling structure.

5. A sub-housing as claimed in claim 1, further including an inlet filter positioned adjacent the gas inlet and an outlet muffler positioned adjacent the gas outlet.

6. A sub-housing as claimed in claim 1, wherein the gas inlet has a cross-sectional dimension that is larger than a cross-sectional dimension of the gas outlet.

7. A sub-housing as claimed in claim 1, wherein the impeller and the shaft are engaged at a position that is external to the gas flow path.

\* \* \* \* \*